(12) United States Patent
Tone et al.

(10) Patent No.: US 11,033,506 B2
(45) Date of Patent: Jun. 15, 2021

US011033506B2

(54) EXTERNAL SKIN PREPARATION COMPRISING A CORE-SHELL STRUCTURE

(71) Applicant: SEKISUI CHEMICAL CO., LTD., Osaka (JP)

(72) Inventors: Saori Tone, Osaka (JP); Takayuki Akamine, Osaka (JP); Daichi Kawamura, Osaka (JP); Yuuta Nakamura, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/756,097

(22) PCT Filed: Nov. 20, 2018

(86) PCT No.: PCT/JP2018/042818
§ 371 (c)(1),
(2) Date: Apr. 14, 2020

(87) PCT Pub. No.: WO2019/102992
PCT Pub. Date: May 31, 2019

(65) Prior Publication Data
US 2020/0281862 A1 Sep. 10, 2020

(30) Foreign Application Priority Data

Nov. 21, 2017 (JP) .............................. JP2017-223589
May 24, 2018 (JP) .............................. JP2018-099408
Oct. 30, 2018 (JP) .............................. JP2018-203565

(51) Int. Cl.
| *A61K 9/50* | (2006.01) |
| *A61K 9/00* | (2006.01) |
| *A61K 31/4402* | (2006.01) |
| *A61K 31/496* | (2006.01) |
| *A61K 47/12* | (2006.01) |
| *A61K 47/40* | (2006.01) |

(52) U.S. Cl.
CPC .............. *A61K 9/50* (2013.01); *A61K 9/0014* (2013.01); *A61K 31/4402* (2013.01); *A61K 31/496* (2013.01); *A61K 47/12* (2013.01); *A61K 47/40* (2013.01)

(58) Field of Classification Search
CPC .......... A61K 9/50; A61K 9/00; A61K 31/496; A61K 47/12; A61K 47/40; A61K 47/38; A61K 47/26; A61K 47/36; A61P 25/18
See application file for complete search history.

(56) References Cited

U.S. PATENT DOCUMENTS

| 2004/0077594 A1* | 4/2004 | Nerurkar ............... A61K 31/496 514/58 |
| 2006/0194973 A1 | 8/2006 | Gainer et al. |
| 2006/0234979 A1 | 10/2006 | Nerurkar et al. |
| 2007/0141161 A1 | 6/2007 | Shaw et al. |
| 2007/0148252 A1 | 6/2007 | Shaw et al. |
| 2009/0186903 A1 | 7/2009 | Nerurkar et al. |
| 2009/0238846 A1 | 9/2009 | Fujii et al. |
| 2011/0160224 A1 | 6/2011 | Nerurkar et al. |
| 2011/0236487 A1 | 9/2011 | Shaw et al. |
| 2012/0052098 A1 | 3/2012 | Shaw et al. |
| 2012/0053145 A1 | 3/2012 | Nerurkar et al. |
| 2012/0095099 A1 | 4/2012 | Gainer et al. |
| 2012/0184563 A1 | 7/2012 | Hanma |
| 2013/0045981 A1 | 2/2013 | Nerurkar et al. |
| 2013/0156821 A1 | 6/2013 | Shaw et al. |

(Continued)

FOREIGN PATENT DOCUMENTS

| EP | 2 298 282 A1 | 3/2011 |
| JP | 2002-193790 A | 7/2002 |

(Continued)

OTHER PUBLICATIONS

Uekama, Kaneto, "Special edition/ Release control technology and incense product development, Control of drug release by cyclodextrin", Fragrance Journal, 1991, vol. 19, No. 3, pp. 22-27.
International Search Report for the Application No. PCT/JP2018/042818 dated Feb. 5, 2019.
Written Opinion of the International Searching Authority (PCT/ISA/237) for the Application No. PCT/JP2018/042818 dated Feb. 5, 2019.
Written Opinion of the International Searching Authority (PCT/ISA/237) for the Application No. PCT/JP2018/042818 dated Feb. 5, 2019 (English Translation dated Jun. 4, 2020).

*Primary Examiner* — Carlos A Azpuru
(74) *Attorney, Agent, or Firm* — Cheng Law Group, PLLC

(57) ABSTRACT

Provided is an external skin preparation capable of enhancing permeability of an active ingredient into parts of the epidermis located below the stratum corneum and the dermis even when a poorly water-soluble active ingredient is used. There is provided an external skin preparation containing a core-shell structure, comprising a core portion containing a poorly water-soluble active ingredient and a solubilizing agent, and a shell portion containing a surfactant. The solubilizing agent is at least one selected from the group consisting of cyclodextrin, methyl-cyclodextrin, dimethyl-cyclodextrin, 2-hydroxypropyl-cyclodextrin, hydroxyethyl-cyclodextrin, sulfobutyl ether-cyclodextrin, glucosyl-cyclodextrin, maltosyl-cyclodextrin and cluster dextrin. The surfactant is at least one selected from the group consisting of glycerol fatty acid esters, sorbitan fatty acid esters, propylene glycol fatty acid esters and fatty acid alkanolamides. A mass ratio between the poorly water-soluble active ingredient and the solubilizing agent (poorly water-soluble active ingredient:solubilizing agent) is 1:0.1 to 1:30.

2 Claims, 3 Drawing Sheets

(56) References Cited

U.S. PATENT DOCUMENTS

| | | |
|---|---|---|
| 2013/0287851 A1 | 10/2013 | Shaw et al. |
| 2014/0154309 A1 | 6/2014 | Shaw et al. |
| 2014/0221321 A1 | 8/2014 | Reeder et al. |
| 2014/0235574 A1 | 8/2014 | Nerurkar et al. |
| 2015/0313843 A1 | 11/2015 | Shaw et al. |
| 2015/0328335 A1 | 11/2015 | Nerurkar et al. |
| 2016/0199490 A1 | 7/2016 | Gainer et al. |
| 2017/0079990 A1 | 3/2017 | Reeder et al. |
| 2017/0079991 A1 | 3/2017 | Reeder et al. |
| 2017/0165279 A1 | 6/2017 | Reeder et al. |
| 2017/0202855 A1 | 7/2017 | Shaw et al. |
| 2018/0071208 A1 | 3/2018 | Shim et al. |
| 2018/0085565 A1 | 3/2018 | Kang et al. |
| 2018/0271979 A1 | 9/2018 | Gainer et al. |
| 2019/0015431 A1 | 1/2019 | Reeder et al. |
| 2019/0117673 A1 | 4/2019 | Shaw et al. |
| 2019/0117674 A1 | 4/2019 | Shaw et al. |

FOREIGN PATENT DOCUMENTS

| | | |
|---|---|---|
| JP | 2006-501240 A | 1/2006 |
| JP | 2008-195712 A | 8/2008 |
| JP | 2008-531582 A | 8/2008 |
| JP | 2009-524582 A | 7/2009 |
| JP | 4843494 B2 | 12/2011 |
| JP | 2014-88453 A | 5/2014 |
| JP | 2016-507526 A | 3/2016 |
| WO | WO-2010/146872 A1 | 12/2010 |
| WO | WO-2016/163752 A1 | 10/2016 |

* cited by examiner

[FIG. 1]
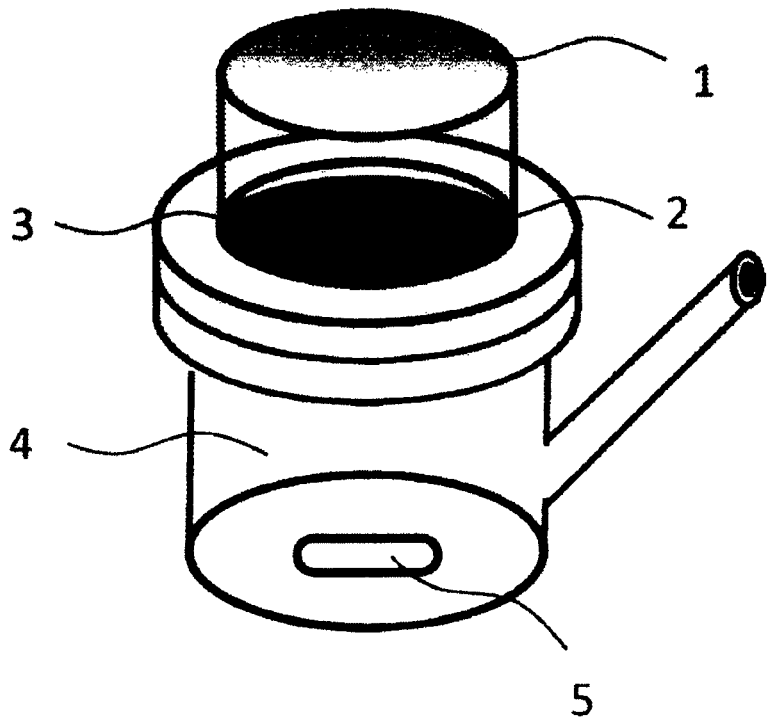
[FIG. 2]
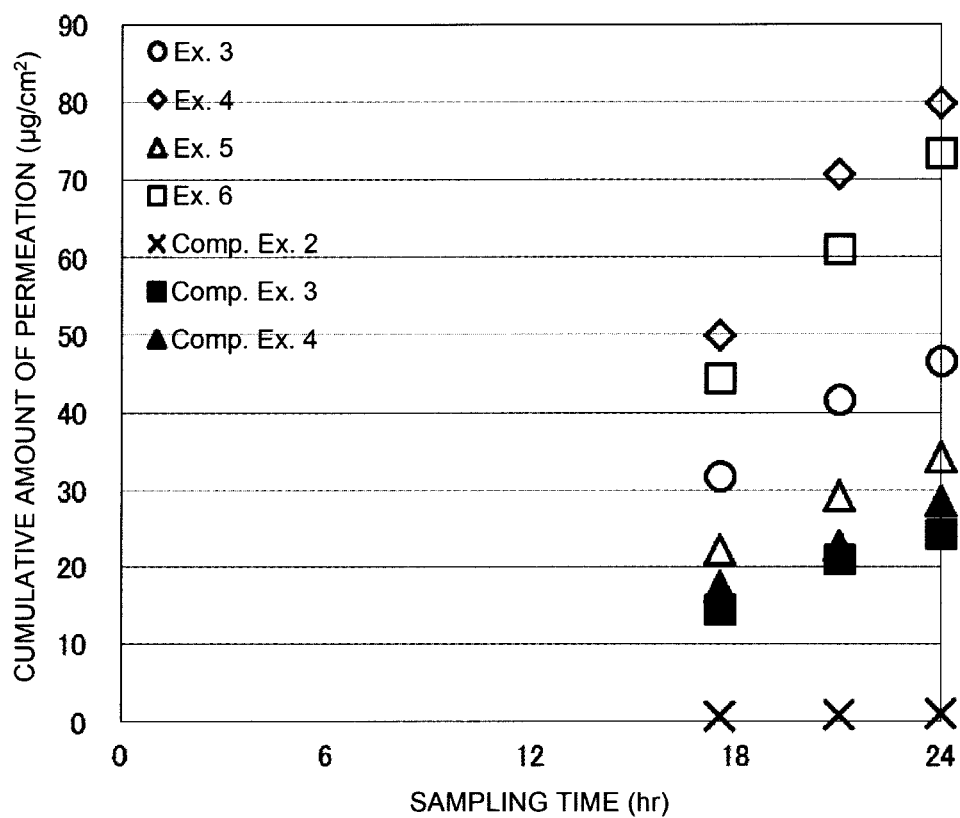

[FIG. 3]
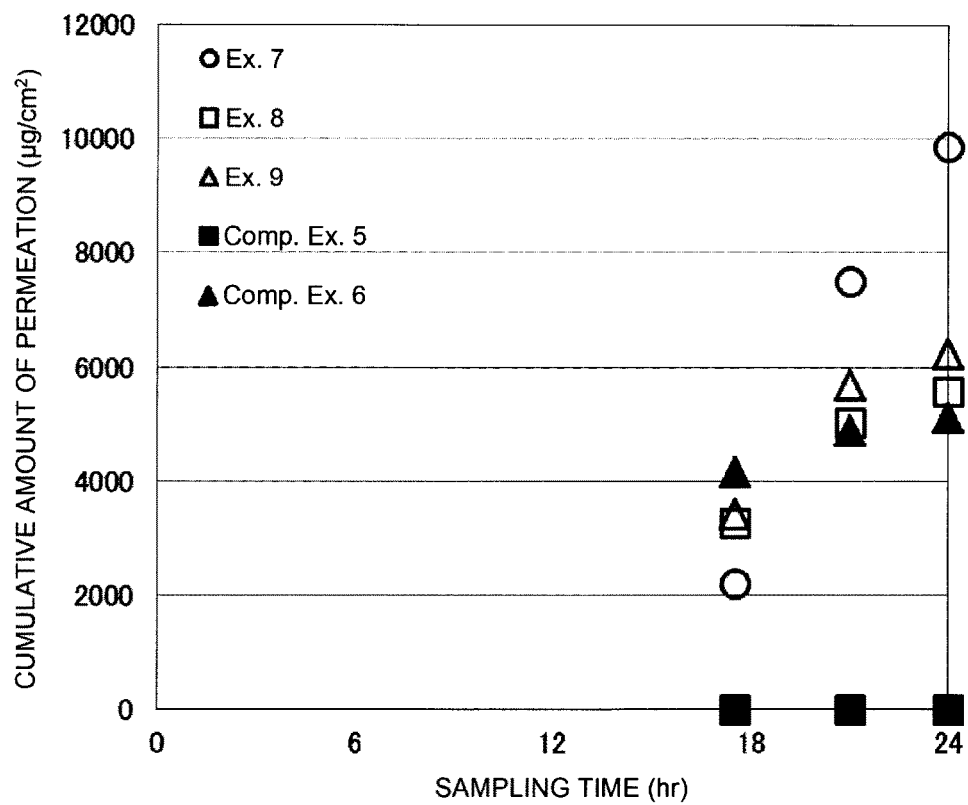
[FIG. 4]
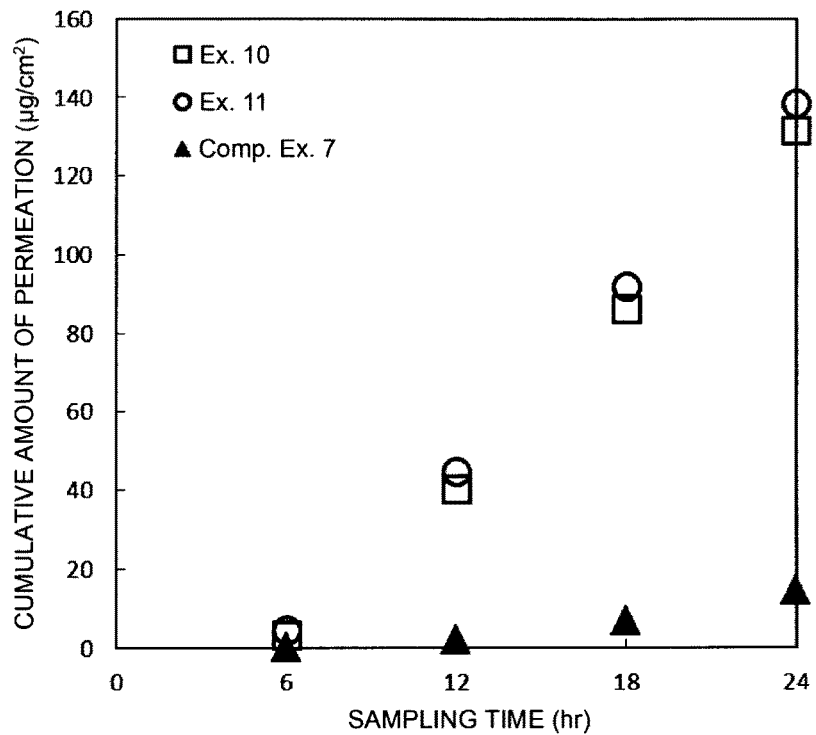

[FIG. 5]
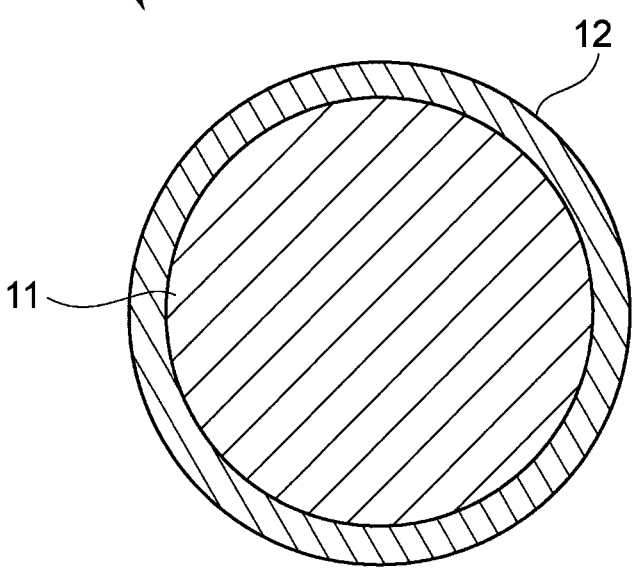

EXTERNAL SKIN PREPARATION COMPRISING A CORE-SHELL STRUCTURE

TECHNICAL FIELD

The present invention relates to an external skin preparation containing a poorly water-soluble active ingredient.

BACKGROUND ART

Conventionally, external skin preparations capable of allowing active ingredients such as drugs to be transdermally absorbed have been known. For these, since the skin has hydrophobic stratum corneum, various studies on microneedle method, S/O (Solid-in-Oil) method and other methods have been made in order to allow the active ingredients to be transdermally absorbed.

For example, in Patent Literature 1, an S/O type external preparation in which a drug-containing composite is dissolved or dispersed in an oil phase is disclosed. It is described that the drug-containing composite is a solid in which a hydrophilic drug is covered with a surfactant. In Patent Literature 1, it is described that such an S/O type external preparation is excellent in transdermal absorbability.

CITATION LIST

Patent Literature

Patent Literature 1: Japanese Patent No. 4843494

SUMMARY OF INVENTION

Technical Problem

The present inventors have found that because parts of the epidermis located below the stratum corneum (living epidermis) and the dermis are hydrophilic, a problem of a poorly water-soluble active ingredient used is that the active ingredient does not easily permeate the living epidermis below the stratum corneum and the dermis. Specifically, the present inventors have found that in order to allow an active ingredient to permeate the hydrophilic living epidermis and dermis, it is necessary to use an active ingredient having a certain degree of hydrophilicity as in Patent Literature 1. When a poorly water-soluble active ingredient is used, the active ingredient does not easily permeate the living epidermis below the stratum corneum and the dermis, as described above, so that it has been difficult to enhance transdermal absorbability of the poorly water-soluble active ingredient.

It is an object of the present invention to provide an external skin preparation capable of enhancing permeability of an active ingredient into parts of the epidermis located below the stratum corneum and the dermis even when a poorly water-soluble active ingredient is used.

Solution to Problem

As a result of earnest studies, the present inventors have found that an external skin preparation containing a poorly water-soluble active ingredient and a specific solubilizing agent can solve the above problem, and have accomplished the present invention.

Specifically, the external skin preparation according to the present invention is an external skin preparation containing a poorly water-soluble active ingredient and a solubilizing agent, wherein the solubilizing agent is at least one selected from the group consisting of water-soluble polymers, water-soluble saccharides, water-soluble surfactants and aromatic carboxylic acids.

In a specific aspect of the external skin preparation of the present invention, the solubilizing agent is the water-soluble saccharide. Preferably, the water-soluble saccharide is at least one selected from the group consisting of cyclodextrin, cyclodextrin derivatives, dextrin derivatives and cellulose derivatives.

In another specific aspect of the external skin preparation of the present invention, the external skin preparation further comprises a release promoting agent for promoting release of the poorly water-soluble active ingredient.

In a further specific aspect of the external skin preparation of the present invention, the external skin preparation is combined with a means of permeation into stratum corneum.

In a still further specific aspect of the external skin preparation of the present invention, the means of permeation into stratum corneum is at least one selected from the group consisting of an S/O (Solid in Oil) technique, a microneedle, PassPort System, iontophoresis, electroporation, thermal poration, sonophoresis and a needleless syringe.

Advantageous Effects of Invention

According to the present invention, an external skin preparation can be provided that is capable of enhancing permeability of an active ingredient into parts of the epidermis located below the stratum corneum (living epidermis) and the dermis even when a poorly water-soluble active ingredient is used.

BRIEF DESCRIPTION OF DRAWINGS

FIG. 1 is a schematic view of a cell for a test of drug permeation into the skin.

FIG. 2 is a view showing a graph of results of the cumulative amounts of permeation in Examples 3 to 6 and Comparative Examples 2 to 4.

FIG. 3 is a view showing a graph of results of the cumulative amounts of permeation in Examples 7 to 9 and Comparative Examples 5 and 6.

FIG. 4 is a view showing a graph of results of the cumulative amounts of permeation in Examples 10 and 11 and Comparative Example 7.

FIG. 5 is a schematic sectional view showing one example of a core-shell structure.

DESCRIPTION OF EMBODIMENTS

Details of the present invention will be described hereinafter.

The external skin preparation of the present invention contains a poorly water-soluble active ingredient and a solubilizing agent. The poorly water-soluble active ingredient is an active ingredient having a solubility of less than 0.1 mass % in pure water at 25° C. The solubilizing agent is an ingredient for solubilizing the poorly water-soluble active ingredient in water. The solubilizing agent is at least one selected from the group consisting of water-soluble polymers, water-soluble saccharides, water-soluble surfactants and aromatic carboxylic acids.

In the present invention, by solubilizing the poorly water-soluble active ingredient by the solubilizing agent, the solubility of the poorly water-soluble active ingredient in pure water at 25° C. is preferably enhanced to not less than 0.1 mass %. The solubility is a solubility of the poorly water-soluble active ingredient in 100 mass % of pure water.

In the external skin preparation of the present invention, by solubilizing the poorly water-soluble active ingredient in water by the solubilizing agent as described above, the solubility of the poorly water-soluble active ingredient in water is enhanced. Conventionally, the poorly water-soluble active ingredient does not easily permeate the hydrophilic living epidermis located below the stratum corneum and the dermis, that is, the skin from which the stratum corneum has been removed. The ratio of permeation of a poorly water-soluble active ingredient into the skin from which the stratum corneum has been removed, that is, the utilization ratio of an active ingredient is, for example, less than 2%. It has been found that in the present invention, by combining the solubilizing agent with such a poorly water-soluble active ingredient, the permeability of an active ingredient into the skin from which the stratum corneum has been removed is enhanced.

In other words, by combining the solubilizing agent with the poorly water-soluble active ingredient, the external skin preparation of the present invention has a permeation means to allow the active ingredient to permeate the hydrophilic living epidermis located below the stratum corneum and the dermis. On that account, even in the hydrophilic living epidermis located below the stratum corneum and the dermis, permeability of the poorly water-soluble active ingredient can be enhanced. Accordingly, in the external skin preparation of the present invention, transdermal absorbability of the poorly water-soluble active ingredient can be further enhanced. The "living epidermis" refers to "parts of the epidermis located below the stratum corneum", that is, "parts of the epidermis other than the stratum corneum".

In the present invention, the solubility of the poorly water-soluble active ingredient having been solubilized by the solubilizing agent, in pure water at 25° C. is more preferably not less than 0.1 mass %, still more preferably not less than 0.5 mass %. In this case, permeability of the poorly water-soluble active ingredient in the living epidermis below the stratum corneum and the dermis can be further enhanced. The upper limit of the solubility of the poorly water-soluble active ingredient having been solubilized by the solubilizing agent, in pure water at 25° C. is not particularly limited, but in view of properties of the material, the solubility can be, for example, not more than 100 mass %.

In the present invention, the external skin preparation preferably further contains a release promoting agent. The release promoting agent is an active ingredient release promoting agent for promoting release of the poorly water-soluble active ingredient into the body. By using the release promoting agent, transdermal absorbability of the poorly water-soluble active ingredient can be further enhanced. Examples of such release promoting agents include, but are not particularly limited to, lactic acid, tartaric acid, urea, glycerol, sorbitol, ethylene glycol and propylene glycol. Of these, release promoting agents having a plurality of hydrophilic functional groups are lactic acid, tartaric acid, urea, glycerol and sorbitol. Examples of release promoting agents which are polybasic acids include lactic acid, tartaric acid, sulfuric acid, citric acid, oxalic acid and phosphoric acid. Examples of release promoting agents which are polyhydric alcohols include glycerol, sorbitol, ethylene glycol and propylene glycol.

The external skin preparation of the present invention may have been combined with a means of permeation into stratum corneum. Examples of the means of permeation into stratum corneum include an S/O (Solid in Oil) technique, a microneedle, PassPort System, iontophoresis, electroporation, thermal poration, sonophoresis and a needleless syringe. These may be used singly, or a plurality of them may be used in combination. By using such a means of permeation into stratum corneum, permeability of the poorly water-soluble active ingredient can be further enhanced even in the stratum corneum. Hence, the permeability of the poorly water-soluble active ingredient in the whole skin, namely, the epidermis including the stratum corneum and the dermis can be further enhanced, and the transdermal absorbability can be further enhanced.

Constitution of the external skin preparation of the present invention will be described in more detail hereinafter.

(Poorly Water-Soluble Active Ingredient)

The poorly water-soluble active ingredient may be one showing any solubility of "very slightly soluble" and "practically insoluble", which are terms for solubilities in the Japanese Pharmacopeia, and is an active ingredient having a solubility of less than 0.1 mass % in pure water at 25° C. In this context, this solubility is a solubility of the poorly water-soluble active ingredient in pure water before being solubilized. The poorly water-soluble active ingredient is sometimes referred to as an active ingredient simply hereinafter.

An octanol/water partition coefficient of the active ingredient can be, for example, −2 to 6. In the present invention, the octanol/water partition coefficient is determined based on an active ingredient concentration of each phase when adding an active ingredient to a flask containing octanol and an aqueous buffer solution of pH 7, and shaking the flask. Specifically, the octanol/water partition coefficient can be determined by calculation using an equation: Octanol/water partition coefficient=$\text{Log}_{10}$ (concentration in an octanol phase/concentration in an aqueous phase).

The active ingredient is not particularly limited as long as it is an ingredient having physiological activity. Preferably, the active ingredient is an ingredient compounded for the purpose of exhibiting its physiological activity. In a preferred embodiment thereof, an ingredient which has physiological activity but is not compounded for the purpose of exhibiting its physiological activity in view of the amount compounded, the compounding method, etc. is not included in the active ingredients. Examples of the active ingredients include ingredients compounded in medicines as active ingredients.

As the active ingredients compounded in medicines, any of those required to have a systematic action and those required to have a local action can be used.

Specific examples of the active ingredients compounded in medicines include, but are not particularly limited to, dementia therapeutic agents, anti-schizophrenia drugs, anti-epileptic agents, antidepressants, antiparkinsonian agents, anti-allergic agents, anticancer agents, antidiabetics, antihypertensive agents, erectile dysfunction drugs, skin disease therapeutic agents, local analgesics, and pharmaceutically acceptable salts thereof. More specific examples of the above-mentioned poorly water-soluble active ingredients include aripiprazole, lorazepam, oxazolam, phenytoin, phenobarbital, carbamazepine, primidone, nitrazepam, clonazepam, lofepramine, amoxapine, mazindol, escitalopram, bupropion, levomepromazine, propericiazine, haloperidol, bromperidol, pimozide, sulpiride, zotepine, zonisamide, bromocriptine, metadoxine, gliclazide, nateglinide, pioglitazone, vorinostat, mirabegron, cilnidipine, felodipine, manidipine, digoxin, ubidecarenone, oxendolone, flutamide, nilvadipine, trandolapril, valsartan, candesartan cilexetil, carvedilol, bunazosin, reserpine, deserpidine, clinofibrate, pemafibrate and tadalafil. These active ingredients may be acidic, may be neutral, or may be basic.

The pharmaceutically acceptable salt is not particularly limited, and any of acid salts and basic salts can be adopted. Examples of the acid salts include inorganic acid salts, such as hydrochloride, hydrobromide, sulfate, nitrate and phosphate, and organic acid salts, such as acetate, propionate, tartrate, fumarate, maleate, malate, citrate, methanesulfonate, benzenesulfonate and p-toluenesulfonate. Examples of the basic salts include alkali metal salts, such as sodium salts and potassium salts, and alkaline earth metal salts, such as calcium salts and magnesium salts.

A molecular weight of the active ingredient is preferably not less than 50 g/mol, more preferably not less than 100 g/mol, still more preferably not less than 200 g/mol. In view of further enhancement in transdermal absorbability of the active ingredient, the molecular weight of the active ingredient is preferably not more than 5000 g/mol, more preferably not more than 2000 g/mol, still more preferably not more than 1000 g/mol.

(Solubilizing Agent)

The solubilizing agent is an ingredient for solubilizing the poorly water-soluble active ingredient in water. By the presence of this solubilizing agent, the solubility of the poorly water-soluble active ingredient in pure water at 25° C. is preferably enhanced to not less than 0.1 mass %.

Therefore, the solubilizing agent is not particularly limited as long as it has such a function as above. As the solubilizing agent, for example, any of water-soluble polymers, water-soluble saccharides, water-soluble surfactants and aromatic carboxylic acids can be used. These may be used singly, or a plurality of them may be used in combination. The term water-soluble means that not less than 1 g of a substance dissolves in 100 g of pure water at 25° C. to give a transparent and homogeneous solution.

As the water-soluble polymers, for example, polyvinyl alcohol, polyarginine, polyethyleneimine and carboxyvinyl polymers can be used.

As the water-soluble saccharides, for example, cyclodextrin, cyclodextrin derivatives, cycloamylose, cluster dextrin, hydroxypropyl cellulose, hydroxypropyl methylcellulose, cellulose derivatives of hypromellose acetate succinate and the like, hypromellose phthalate, hypromellose acetate succinate, chitin and chitosan can be used. As the cyclodextrin derivatives, for example, α-cyclodextrin, β-cyclodextrin, γ-cyclodextrin, methyl-β-cyclodextrin, dimethyl-α-cyclodextrin, dimethyl-β-cyclodextrin, dimethyl-γ-cyclodextrin, 2-hydroxypropyl-α-cyclodextrin, hydroxyethyl-β-cyclodextrin, 2-hydroxypropyl-β-cyclodextrin, 2-hydropropyl-γ-cyclodextrin, sulfobutyl ether-α-cyclodextrin, sulfobutyl ether-β-cyclodextrin, sulfobutyl ether-γ-cyclodextrin, glucosyl-α-cyclodextrin, glucosyl-β-cyclodextrin, glucosyl-γ-cyclodextrin, maltosyl-α-cyclodextrin, maltosyl-β-cyclodextrin and maltosyl-γ-cyclodextrin can be used.

As the water-soluble surfactants, for example, sucrose fatty acid esters, such as sucrose laurate, sucrose myristate and sucrose stearate, glycerol fatty acid esters, sorbitan fatty acid esters, propylene glycol fatty acid esters, fatty acid esters, fatty alcohol ethoxylates, polyoxyethylene alkyl ethers, polyoxyethylene alkyl phenyl ethers, alkyl glucosides and polyoxyethylene castor oil can be used. A weighted average value of HLB values of the water-soluble surfactants is preferably not less than 14. Determination of the HLB value will be described later.

As the aromatic carboxylic acids, for example, gallic acid, 4-aminobenzoic acid, mellitic acid, benzoic acid, phthalic acid, isophthalic acid, terephthalic acid, salicylic acid, cinnamic acid, 2-hydroxybenzoic acid and hibenzic acid can be used.

In view of further enhancement in permeability of the poorly water-soluble active ingredient in the epidermis below the stratum corneum and the dermis, the solubilizing agent is preferably a water-soluble saccharide. More preferably, the water-soluble saccharide is at least one selected from the group consisting of cyclodextrin, cyclodextrin derivatives and dextrin derivatives.

A molecular weight of the solubilizing agent is preferably not less than 100 g/mol, more preferably not less than 500 g/mol, still more preferably not less than 1000 g/mol, and is preferably not more than 50000 g/mol, more preferably not more than 20000 g/mol, still more preferably not more than 10000 g/mol. When the solubilizing agent has a molecular weight of not less than the above lower limit, it is possible for, for example, cyclodextrin to include an active ingredient having a much higher molecular weight. When the molecular weight of the solubilizing agent is not more than the above upper limit, the solubilizing agent can be allowed to more certainly permeate the skin together with the active ingredient.

A mass ratio between the poorly water-soluble active ingredient and the solubilizing agent (poorly water-soluble active ingredient:solubilizing agent) is not particularly limited. However, the mass ratio therebetween (poorly water-soluble active ingredient:solubilizing agent) is preferably 1:0.1 to 1:30, more preferably 1:0.5 to 1:10. When the mass ratio (poorly water-soluble active ingredient:solubilizing agent) is in the above range, solubility of the poorly water-soluble active ingredient in water can be further enhanced, and besides, permeability of the poorly water-soluble active ingredient in the epidermis below the stratum corneum and the dermis can be further enhanced.

(Release Promoting Agent)

The external skin preparation of the present invention may further contain a release promoting agent. The release promoting agent is for promoting release of the active ingredient in the body, i.e., is a release promoting agent for an active ingredient. By using the release promoting agent, permeability of the poorly water-soluble active ingredient into the epidermis below the stratum corneum and the dermis can be further enhanced.

A water solubility of the release promoting agent is preferably not less than 5 mass %. In this case, transdermal absorbability of the poorly water-soluble active ingredient can be further enhanced. In view of further enhancement in the transdermal absorbability, the water solubility of the release promoting agent is more preferably not less than 10 mass %, and is preferably not more than 500 mass %, more preferably not more than 300 mass %. The water solubility refers to a solubility in 100 mass % of water.

The release promoting agent preferably has a hydrophilic functional group. Examples of the hydrophilic functional groups include hydroxyl group, amino group, carboxyl group, phosphoric acid group and sulfonic acid group. These may be used singly, or a plurality of them may be used in combination. In the present invention, however, the release promoting agent preferably has a plurality of functional groups in view of further enhancement in the transdermal absorbability of the active ingredient. Above all, the release promoting agent is preferably a polybasic acid or a polyhydric alcohol.

Examples of the release promoting agents having a hydrophilic functional group include, but are not particularly limited to, urea, glycerol, sorbitol, lactic acid, tartaric acid, ethylene glycol, propylene glycol and sodium hydroxide. Among them, the release promoting agents having a plurality of hydrophilic functional groups are urea, glycerol, sorbitol, lactic acid and tartaric acid. Examples of the release promoting agents which are polybasic acids include lactic acid, tartaric acid, sulfuric acid, citric acid, oxalic acid and phosphoric acid. Preferred are lactic acid, tartaric acid and citric acid. Examples of the release promoting agents which are polyhydric alcohols include glycerol, sorbitol, ethylene glycol and propylene glycol.

Although a molecular weight of the release promoting agent is not particularly limited, it is preferably not more than 1000000, more preferably not more than 100000, and is preferably not less than 50, more preferably not less than 100. In this case, transdermal absorbability of the active ingredient can be further enhanced.

In the present invention, a mass ratio between the active ingredient and the release promoting agent (active ingredient:release promoting agent) is preferably in the range of 1:0.1 to 1:100. In this case, transdermal absorbability of the active ingredient can be further enhanced. In view of further enhancement in the transdermal absorbability of the active ingredient, the mass ratio (release promoting agent:active ingredient) is preferably 1:0.1 to 1:50, more preferably 1:0.5 to 1:30.

(Other Additive Ingredients)

The external skin preparation of the present invention may further contain at least one other ingredient. Examples of the other ingredients include, but are not particularly limited to, a stabilizing agent, a transdermal absorption promoting agent, a skin stimulation reducing agent, an antiseptic and an analgesic.

The stabilizing agent has an action of stabilizing a particle structure. Moreover, the stabilizing agent prevents unintentional early disintegration of the particle structure, and plays a role in further enhancing a sustained releasing effect of the active ingredient.

Examples of the stabilizing agents include, but are not particularly limited to, polysaccharides, proteins and hydrophilic polymer materials. One or more of the stabilizing agents may be contained. The content of the stabilizing agent can be appropriately set depending on the type thereof. For example, the stabilizing agent can be compounded in such a manner that the mass ratio between the active ingredient and the stabilizing agent (active ingredient:stabilizing agent) is 1:0.1 to 1:100.

Examples of the transdermal absorption promoting agents include, but are not particularly limited to, higher alcohols, N-acyl sarcosine and salts thereof, higher monocarboxylic acids, higher monocarboxylic acid esters, aromatic monoterpene fatty acid esters, divalent carboxylic acids having 2 to 10 carbon atoms and salts thereof, polyoxyethylene alkyl ether phosphoric acid esters and salts thereof, lactic acid, lactic acid esters, and citric acid. These transdermal absorption promoting agents may be used singly, or a plurality of them may be used in combination. The content of the transdermal absorption promoting agent can be appropriately set depending on the type thereof. For example, the transdermal absorption promoting agent can be compounded in such a manner that the mass ratio between the active ingredient and the transdermal absorption promoting agent (active ingredient:transdermal absorption promoting agent) is 1:0.01 to 1:100.

Examples of the skin stimulation reducing agents include, but are not particularly limited to, hydroquinone glycosides, pantethine, tranexamic acid, lecithin, titanium oxide, aluminum hydroxide, sodium nitrite, sodium hydrogen nitrite, soybean lecithin, methionine, glycyrrhetinic acid, BHT, BHA, vitamin E and derivatives thereof, vitamin C and derivatives thereof, benzotriazole, propyl gallate, and mercaptobenzimidazole. These skin stimulation reducing agents may be used singly, or a plurality of them may be used in combination. The content ratio of the skin stimulation reducing agent can be appropriately set depending on the type thereof. The skin stimulation reducing agent can be compounded in such a manner that the content thereof is, for example, 0.01 mass % to 50 mass % based on the whole external skin preparation.

Examples of the antiseptics include, but are not particularly limited to, methyl paraoxybenzoate, propyl paraoxybenzoate, phenoxy ethanol, and thymol. These antiseptics may be used singly, or a plurality of them may be used in combination. The content ratio of the antiseptic can be appropriately set depending on the type thereof. The antiseptic can be compounded in such a manner that the content thereof is, for example, 0.01 mass % to 10 mass % based on the whole external skin preparation.

Examples of the analgesics include, but are not particularly limited to, local anesthetics, such as procaine, tetracaine, lidocaine, dibucaine and prilocaine, and salts thereof. These analgesics may be used singly, or a plurality of them may be used in combination. The content ratio of the analgesic can be appropriately set depending on the type thereof. The analgesic can be compounded in such a manner that the content thereof is, for example, 0.01 mass % to 30 mass % based on the whole external skin preparation.

(Stratum Corneum Permeation Means)

The external skin preparation of the present invention may be combined with a means of permeation into stratum corneum. Examples of the means of permeation into stratum corneum include an S/O (Solid in Oil) technique, a microneedle, PassPort System, iontophoresis, electroporation, thermal poration, sonophoresis or a needleless syringe. These may be used singly, or a plurality of them may be used in combination. By using such a means of permeation into stratum corneum, permeability of the poorly water-soluble active ingredient can be further enhanced even in the stratum corneum. Hence, the permeability of the poorly water-soluble active ingredient in the whole skin, that is, the epidermis including the stratum corneum and the dermis, can be further enhanced, and the transdermal absorbability can be further enhanced.

Details of the external skin preparation combined with the S/O technique as one example of the means of permeation into stratum corneum will be described below.

(S/O Technique)

The external skin preparation combined with the S/O technique has a core-shell structure and a base phase which is an oil phase. The core-shell structure is dispersed or dissolved in the base phase which is an oil phase.

Core-Shell Structure;

The core-shell structure includes a core portion containing an active ingredient and a solubilizing agent and a shell portion containing a surfactant.

The core portion and the shell portion may be bonded to each other by intermolecular force or the like to form an aggregate. However, in view of further enhancement in transdermal absorbability of the active ingredient, at least a part of the surface of the core portion is preferably covered with the shell portion.

More specifically, not less than 30% of the surface of the core portion is preferably covered with the shell portion. More preferably not less than 50%, still more preferably not less than 70%, much more preferably not less than 85%, particularly preferably not less than 95%, most preferably not less than 99% of the surface is covered. The surface of the core portion may be completely covered with the shell portion. The core-shell structure has such a constitution as above, and therefore, when it is applied to, for example, the skin, the active ingredient contained in the core portion can be released into the body.

One example of the core-shell structure will be described below with reference to the drawing.

FIG. 5 is a schematic sectional view showing one example of the core-shell structure.

As shown in FIG. 5, a core-shell structure 10 includes a core portion 11 and a shell portion 12. The surface of the core portion 11 is covered with the shell portion 12.

However, the shape of the core-shell structure is not limited to such a spherical particle. The core-shell structure may be a particle having a rod-like, cubic, lens-like, micellar, lamellar, hexagonal, bicellar, sponge-like or sea urchin-like shape, or may be amorphous. As described above, the shape of the core-cell structure is not particularly limited. However, at least a part of the surface of the core portion is preferably covered with the shell portion, as previously described.

In the present embodiment, the core portion is a solid. Since the core portion is a solid, the stability in the base phase can be further improved. Moreover, since such a core-shell structure is dispersed in the base phase which is an oil phase, an external skin preparation having an S/O (Solid in Oil) type structure is formed.

As described in the production process mentioned later, the core-shell structure is obtained by drying a W/O emulsion to remove the solvent (aqueous solvent and oil solvent), and therefore, the core portion is a solid (S in the above S/O (Solid in Oil) type).

Although the shape and the size of the core-shell structure are not particularly limited, the number-average particle diameter is preferably 0.5 nm to 500 nm, more preferably 1 nm to 300 nm, still more preferably 1 nm to 100 nm. In the present invention, the number-average particle diameter of the core-shell structure is a number-average particle diameter calculated by, for example, a dynamic light scattering method in dispersing in a solvent such as squalane.

Core Portion;

In the core-shell structure, the core portion contains an active ingredient. The active ingredient contained in the core portion is the aforesaid poorly water-soluble active ingredient (the poorly water-soluble active ingredient is sometimes referred to as an active ingredient simply hereinafter). The aforesaid solubilizing agent is also contained in the core portion. In the core portion, the aforesaid stabilizing agent, transdermal absorption promoting agent, skin stimulation reducing agent, antiseptic or analgesic, etc. may be contained.

Shell Portion;

In the core-shell structure, the shell portion contains a surfactant. The surfactant is not particularly limited as long as it is a surfactant capable of forming the shell portion of the core-shell structure.

In the present invention, the HLB (Hydrophile Lypophile Balance) value of the surfactant is preferably not less than 4. The HLB value is an index showing that an emulsifying agent is hydrophilic or lipophilic, and a larger HLB value indicates a higher hydrophilicity. In the present invention, since the HLB value of the surfactant is not less than 4, the transdermal absorbability of the active ingredient has been enhanced.

In the present invention, the HLB value is calculated by the following Griffin equation.

$$\text{HLB value} = 20 \times \{(\text{molecular weight of hydrophilic moiety})/(\text{total molecular weight})\}$$

When a plurality of surfactants are contained, the HLB value is a weighted average value of HLB values.

The weighted average value of the HLB values can be calculated using, for example, the following calculation equation.

When surfactant raw materials having HLB values of A, B and C are used, a calculation equation for a weighted average value is $(xA+yB+zC)/(x+y+z)$, wherein x, y and z each represent the weight of the respective core-shell structure for the surfactant raw materials having the HLB values of A, B and C.

In view of further enhancement in transdermal absorbability of the active ingredient, the HLB value of the surfactant is preferably not less than 4, more preferably not less than 5. The upper limit of the HLB value of the surfactant can be, for example, 12.

The surfactant may have at least one of a saturated hydrocarbon group such as an alkyl group and an unsaturated hydrocarbon group such as an alkenyl group or an alkynyl group.

The number of carbon atoms in the saturated hydrocarbon group is not less than 7 and not more than 11, preferably not less than 7 and not more than 9. When the number of carbon atoms in the saturated hydrocarbon group is not less than the above lower limit, coverability of the surface of the core portion with the shell portion is further improved. On this account, a core-shell structure exhibiting a higher immediate effect in the transdermal absorption can be obtained. When the number of carbon atoms in the saturated hydrocarbon group is not more than the above upper limit, releasability of the active ingredient from the core-shell structure in the body is further improved, and therefore, a core-shell structure exhibiting a higher immediate effect in the transdermal absorption can be obtained.

The number of carbon atoms in the unsaturated hydrocarbon group is not less than 7 and not more than 17, preferably not less than 7 and not more than 13, more preferably not less than 7 and not more than 11. When the number of carbon atoms in the unsaturated hydrocarbon group is not less than the above lower limit, coverability of the surface of the core portion with the shell portion is further improved. On this account, a core-shell structure exhibiting a higher immediate effect in the transdermal absorption can be obtained. When the number of carbon atoms in the unsaturated hydrocarbon group is not more than the above upper limit, releasability of the active ingredient from the core-shell structure in the body is further improved. Therefore, a core-shell structure exhibiting a higher immediate effect in the transdermal absorption can be obtained.

A molecular weight of the hydrophilic moiety of the surfactant is not less than 100 g/mol and not more than 350 g/mol, preferably not less than 100 g/mol and not more than 300 g/mol, more preferably not less than 100 g/mol and not more than 200 g/mol. When the molecular weight of the hydrophilic moiety of the surfactant is not less than the above lower limit, coverability of the core portion with the shell portion is further improved. On this account, a core-shell structure exhibiting a higher immediate effect in the transdermal absorption can be obtained. When the molecular weight of the hydrophilic moiety of the surfactant is not more than the above upper limit, releasability of the active ingredient from the particle in the body is further improved.

On this account, a core-shell structure exhibiting a higher immediate effect in the transdermal absorption can be obtained.

The surfactant is not particularly limited and can be appropriately selected according to the application. For example, the surfactant can be selected from a wide variety of surfactants employable for medicines and cosmetics. A plurality of surfactants may be used in combination.

The surfactant preferably contains at least one selected from the group consisting of glycerol fatty acid esters, sorbitan fatty acid esters, propylene glycol fatty acid esters and fatty acid alkanolamides. Of these, in view of simultaneously achieving transdermal absorbability and low skin irritation at a much higher level, the surfactant preferably contains at least one selected from the group consisting of glycerol fatty acid esters, sorbitan fatty acid esters and propylene glycol fatty acid esters.

Examples of the glycerol fatty acid esters in the present invention include, but are not particularly limited to, esters of glycerol and fatty acids.

Glycerol may be polyglycerol. Although the degree of polymerization n of polyglycerol is not particularly limited, it is preferably not more than 5, more preferably not more than 4, still more preferably not more than 3. Of these, monoglycerol, diglycerol or triglycerol is preferable as glycerol. Specifically, the glycerol fatty acid ester is preferably a monoglycerol fatty acid ester, a diglycerol fatty acid ester or a triglycerol fatty acid ester. In this case, the immediate effect in the transdermal absorption of the active ingredient can be further enhanced.

Examples of the fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soybean oil and castor oil.

In view of further enhancement in immediate effect and transdermal absorbability of the active ingredient, specific preferred examples of the glycerol fatty acid esters include diglyceryl monostearate (NIKKOL DGMS, manufactured by Nippon Surfactant Industries Co., Ltd.), glyceryl monostearate (NIKKOL MGS-BMV, manufactured by Nippon Surfactant Industries Co., Ltd.), glyceryl monostearate (NIKKOL MGS-AMV, manufactured by Nippon Surfactant Industries Co., Ltd.), glyceryl monostearate (NIKKOL MGS-DEXV, manufactured by Nippon Surfactant Industries Co., Ltd.), glyceryl monostearate (NIKKOL MGS-ASEV, manufactured by Nippon Surfactant Industries Co., Ltd.), glyceryl monostearate (NIKKOL MGS-BSEV, manufactured by Nippon Surfactant Industries Co., Ltd.), glyceryl myristate (MGM, manufactured by Nippon Surfactant Industries Co., Ltd.), glyceryl tri(caprylate/caprate) (NIKKOL TRIESTER F-810, manufactured by Nippon Surfactant Industries Co., Ltd.), glyceryl monooleate (NIKKOL MGO, manufactured by Nippon Surfactant Industries Co., Ltd.), glyceryl monoolivate (NIKKOL MGOL-70, manufactured by Nippon Surfactant Industries Co., Ltd.), diglyceryl monooleate (NIKKOL DGMO-CV, manufactured by Nippon Surfactant Industries Co., Ltd.), diglyceryl monooleate (NIKKOL DGMO-90V, manufactured by Nippon Surfactant Industries Co., Ltd.), monoglyceride caprylate (Sunsoft No. 700P-2-C, manufactured by Taiyo Kagaku Co., Ltd.), monoglyceride caprate (Sunsoft No. 760-C, manufactured by Taiyo Kagaku Co., Ltd.), mono/diglyceride caprate (Sunsoft No. 707-C, manufactured by Taiyo Kagaku Co., Ltd.), diglyceride caprate (Sunfat GDC-S, manufactured by Taiyo Kagaku Co., Ltd.), monoglyceride laurate (Sunsoft No. 750-C, manufactured by Taiyo Kagaku Co., Ltd.), and glyceryl monoundecylenate (NIKKOL MGU, manufactured by Nippon Surfactant Industries Co., Ltd.).

More preferred examples of the glycerol fatty acid esters include glyceryl monooleate (NIKKOL MGO, manufactured by Nippon Surfactant Industries Co., Ltd.), glyceryl monoolivate (NIKKOL MGOL-70, manufactured by Nippon Surfactant Industries Co., Ltd.), diglyceryl monooleate (NIKKOL DGMO-CV, manufactured by Nippon Surfactant Industries Co., Ltd.), diglyceryl monooleate (NIKKOL DGMO-90V, manufactured by Nippon Surfactant Industries Co., Ltd.), monoglyceride caprylate (Sunsoft No. 700P-2-C, manufactured by Taiyo Kagaku Co., Ltd.), monoglyceride caprate (Sunsoft No. 760-C, manufactured by Taiyo Kagaku Co., Ltd.), mono/diglyceride caprate (Sunsoft No. 707-C, manufactured by Taiyo Kagaku Co., Ltd.), diglyceride caprate (Sunfat GDC-S, manufactured by Taiyo Kagaku Co., Ltd.), monoglyceride laurate (Sunsoft No. 750-C, manufactured by Taiyo Kagaku Co., Ltd.), or glyceryl monoundecylenate (NIKKOL MGU, manufactured by Nippon Surfactant Industries Co., Ltd.).

Examples of the sorbitan fatty acid esters in the present invention include, but are not particularly limited to, esters of sorbitan and fatty acids.

Examples of the fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soybean oil and castor oil.

In view of further enhancement in immediate effect and transdermal absorbability of the active ingredient, specific preferred examples of the sorbitan fatty acid esters include sorbitan monostearate (NIKKOL SO-10MV, manufactured by Nippon Surfactant Industries Co., Ltd.), sorbitan trioleate (NIKKOL SO-30V, manufactured by Nippon Surfactant Industries Co., Ltd.), sorbitan sesquioleate (NIKKOL SO-15MV, manufactured by Nippon Surfactant Industries Co., Ltd.), sorbitan monooleate (SO-10V, manufactured by Nippon Surfactant Industries Co., Ltd.), sorbitan monolaurate (NIKKOL SL-10, manufactured by Nippon Surfactant Industries Co., Ltd.), coconut oil fatty acid sorbitan (EMALEX SPC-10, manufactured by Nihon Emulsion Co., Ltd.), and sorbitan laurate (RIKEMAL L-250A, manufactured by RIKEN VITAMIN Co., Ltd.).

Examples of the propylene glycol fatty acid esters in the present invention include, but are not particularly limited to, esters of propylene glycol and fatty acids.

Examples of the fatty acids include caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soybean oil and castor oil.

In view of further enhancement in immediate effect and transdermal absorbability of the active ingredient, specific preferred examples of the propylene glycol fatty acid esters include propylene glycol monostearate (RIKEMAL PS-100, manufactured by RIKEN VITAMIN Co., Ltd.), propylene glycol monostearate (NIKKOL PMS-1CV, manufactured by Nippon Surfactant Industries Co., Ltd.), preferably propylene glycol diisostearate (EMALEX PG-di-IS, manufactured by Nihon Emulsion Co., Ltd.), propylene glycol distearate (EMALEX PG-di-S, manufactured by Nihon Emulsion Co., Ltd.), propylene glycol monolaurate (RIKEMAL PL-100, manufactured by RIKEN VITAMIN Co., Ltd.), propylene glycol monooleate (RIKEMAL PO-100, manufactured by RIKEN VITAMIN Co., Ltd.), propylene glycol dioleate (EMALEX PG-di-O, manufactured by Nihon Emulsion Co., Ltd.), propylene glycol dicaprylate (NIKKOL SEFSOL-228, manufactured by Nippon Surfactant Industries Co., Ltd.), and propylene glycol dilaurate (EMALEX PG-M-L, manufactured by Nihon Emulsion Co., Ltd.).

The fatty acid alkanolamides in the present invention refer to those having a structure in which a R—CO group and two —$CH_2CH_2OH$ groups are bonded to N at the center and represented by a chemical formula of R—CON($CH_2CH_2OH$)$_2$.

Specific examples of the fatty acid alkanolamides include oleic acid diethanolamide, lauric acid diethanolamide, lauric acid monoisopropanolamide, stearic acid diethanolamide, stearic acid monoethanolamide, stearic acid monoisopropanolamide, lauric acid myristic acid diethanolamide, palmitic acid monoethanolamide, coconut oil fatty acid diethanolamide, coconut acid fatty acid monoisopropanolamide, coconut oil fatty acid N-methyl ethanolamide, coconut oil fatty acid monoethanolamide, and palm kernel oil fatty acid diethanolamide. In view of further enhancement in skin permeability, the fatty acid alkanolamides are preferably diethanolamides, such as oleic acid diethanolamide, lauric acid diethanolamide or coconut oil fatty acid diethanolamide.

The surfactant in the present invention may further contain a surfactant other than the glycerol fatty acid esters, the sorbitan fatty acid esters, the propylene glycol fatty acid esters or the fatty acid alkanolamides, and such a surfactant can be appropriately selected according to the application. For example, it can be selected from a wide variety of surfactants employable for medicines and cosmetics. A plurality of surfactants may be used in combination.

The surfactant other than the glycerol fatty acid esters, the sorbitan fatty acid esters, the propylene glycol fatty acid esters and the fatty acid alkanolamides may be any of a nonionic surfactant, an anionic surfactant, a cationic surfactant and an amphoteric surfactant.

Examples of the nonionic surfactants include, but are not particularly limited to, fatty acid esters, fatty alcohol ethoxylates, polyoxyethylene alkyl phenyl ethers, alkyl glycosides, polyoxyethylene castor oil and hydrogenated castor oil.

Examples of the fatty acid esters include, but are not particularly limited to, esters of at least one of glycerol, polyglycerol, polyoxyethylene glycerol, polyoxyethylene, sorbitan, propylene glycol and polyoxyethylene sorbitol with fatty acids, such as caproic acid, caprylic acid, capric acid, lauric acid, myristic acid, palmitic acid, stearic acid, behenic acid, undecylenic acid, ricinoleic acid, oleic acid, linoleic acid, linolenic acid, ricinoleic acid, erucic acid, beef tallow, lard, coconut oil, palm oil, palm kernel oil, olive oil, rapeseed oil, rice bran oil, soybean oil and castor oil.

Examples of the anionic surfactants include alkyl sulfate salts, polyoxyethylene alkyl ether sulfate salts, alkylbenzene sulfonic acid salts, fatty acid salts and phosphoric acid ester salts.

Examples of the cationic surfactants include alkyl trimethylammonium salts, dialkyl dimethylammonium salts, alkyl dimethyl benzyl ammonium salts and amine salts.

Examples of the amphoteric surfactants include alkyl amino fatty acid salts, alkyl betaines and alkyl amine oxides.

The surfactant other than the glycerol fatty acid esters, the sorbitan fatty acid esters, the propylene glycol fatty acid esters or the fatty acid alkanolamides is particularly preferably sucrose fatty acid ester, polyoxyethylene glycerol fatty acid ester, polyoxyethylene sorbitol fatty acid ester, polyoxyethylene castor oil or hydrogenated castor oil.

The surfactant other than the glycerol fatty acid esters, the sorbitan fatty acid esters, the propylene glycol fatty acid esters or the fatty acid alkanolamides may be one having a hydrocarbon chain, such as an alkyl chain, an alkenyl chain or an alkynyl chain.

The above-described surfactants may be used singly, or a plurality of the surfactants may be used in combination.

The amount of the surfactant compounded can be appropriately set within a range where the effect of the present invention is exerted. A weight ratio between the active ingredient and the surfactant (active ingredient:surfactant) is preferably 1:0.5 to 1:100. In this case, transdermal absorbability of the active ingredient can be further enhanced. In view of further enhancement in the transdermal absorbability of the active ingredient, the weight ratio between the active ingredient and the surfactant (active ingredient:surfactant) is more preferably 1:0.5 to 1:50, still more preferably 1:0.5 to 1:30.

In the shell portion, the aforesaid stabilizing agent, transdermal absorption promoting agent, skin stimulation reducing agent, antiseptic or analgesic, etc. may be contained.

In the core-shell structure, the aforesaid release promoting agent may be contained. In a specific example, when an external skin preparation containing a core-shell structure is applied to, for example, the skin to bring the core-shell structure into contact with moisture at the interface between the stratum corneum and the dermis, the release promoting agent dissolves out toward the moisture. On that account, disintegration of the core-shell structure in the dermis is further promoted. Owing to this, releasability of the active ingredient in the dermis can be further enhanced.

In the present invention, the release promoting agent may be contained in any of the core portion and the shell portion, but in view of further promoting disintegration of the core-shell structure and thereby further enhancing releasability of the active ingredient, the release promoting agent is preferably contained in at least the core portion. That is to say, the release promoting agent is preferably contained in only the core portion, or is preferably contained in both the core portion and the shell portion.

Production Process for Solubilizable Product;

The solubilizable product refers to a product wherein the poorly water-soluble active ingredient has become solubilizable in water owing to the presence of the solubilizing agent, and the production process therefor is not particularly restricted as long as it is a process capable of solubilizing the poorly water-soluble active ingredient in water. Owing to the presence of the solubilizing agent, the poorly water-soluble active ingredient preferably exhibits a solubility of not less than 0.1 mass % in pure water at 25° C.

The solubilizable product can be produced by a process including steps of dissolving the active ingredient and the solubilizing agent in a solvent, stirring the solution and drying it. A method for drying the solubilizable product is not particularly limited as long as it is a method capable of removing the solvent, and for example, freeze drying or vacuum drying, preferably freeze drying, can be mentioned.

A method for mixing is not particularly limited as long as it is a method capable of solubilizing the poorly water-soluble active ingredient in water, and for example, grinding/mixing using a ball mill and stirring with a homogenizer or the like can be mentioned.

Production Process for Core-Shell Structure;

The core-shell structure can be produced by, for example, a process including a step of drying a W/O emulsion containing the active ingredient in an aqueous phase.

The W/O emulsion is not particularly limited as long as it is a so-called water-in-oil emulsion, specifically it is an emulsion in which droplets of an aqueous solvent are dispersed in an oil solvent.

The W/O emulsion containing the active ingredient and the solubilizing agent in an aqueous phase can be obtained by mixing an aqueous solvent, such as water or a buffer aqueous solution, containing the active ingredient and the solubilizing agent, and an oil solvent, such as cyclohexane, hexane or toluene, containing the surfactant. In this operation, the active ingredient and the solubilizing agent may be added individually, or may be added in a state of a solubilizable product. The aqueous solvent containing the active ingredient and the solubilizing agent may additionally contain additive ingredients, such as a release promoting agent, a stabilizing agent, an absorption promoting agent or a stimulation reducing agent, when needed. Also, the oil solvent containing the surfactant may contain, in addition to the surfactant, additive ingredients, such as a stimulation reducing agent, an analgesic, an absorption promoting agent or a stabilizing agent, when needed. A method for the mixing is not particularly limited as long as it can form a W/O emulsion, and for example, stirring with a homogenizer or the like can be mentioned.

The condition for the stirring with a homogenizer is, for example, about 5000 to about 50000 rpm, preferably about 10000 to about 30000 rpm.

A mass ratio between the surfactant and the active ingredient (surfactant/active ingredient) in the W/O emulsion is not particularly limited, and is, for example, 2 to 100, preferably 3 to 50, more preferably 5 to 30.

A method for dying the W/O emulsion containing the active ingredient and the solubilizing agent in an aqueous phase is not particularly limited as long as it is a method capable of removing the solvent (aqueous solvent and oil solvent) contained in the emulsion, and for example, freeze drying or vacuum drying, preferably freeze drying, can be mentioned.

In view of further decreasing the number-average particle diameter of the resulting core-shell structure, the process preferably further includes a step of heat-treating the W/O emulsion containing the active ingredient and the solubilizing agent in an aqueous phase or a dried product of the W/O emulsion. The heat treatment temperature is, for example, 30 to 60° C., preferably 35 to 50° C., more preferably 35 to 45° C.

The heat treatment time is appropriately adjusted according to the heat treatment temperature, and is, for example, 1 day to 30 days, preferably 2 days to 15 days, more preferably 3 days to 7 days. When the W/O emulsion is subjected to the heat treatment, the aforesaid drying is carried out after the treatment, whereby a core-shell structure can be obtained.

Examples of other methods to further decrease the number-average particle diameter of the resulting core-shell structure include a method in which the W/O emulsion containing the active ingredient and the solubilizing agent in an aqueous phase or a dried product of the W/O emulsion, after dispersing it in a solvent or the like when necessary, is subjected to filtration through a filter or the like or to centrifugation. In the case of filtration through a filter, a pore diameter of the filter is, for example, not more than 1 µm, preferably not more than 0.2 µm, more preferably not more than 0.1 µm.

Such a core-shell structure may be used as it is, or may be used after it is dispersed in a base phase described below or the like.

Base Phase;

The base phase contains the core-shell structures. In this case, the core-shell structures are dispersed or dissolved in the base phase. The base to form the base phase is not particularly limited, and can be selected from a wide variety of bases employable for external skin preparations.

In the core-shell structure, the core portion is a solid. On that account, by dispersing the core-shell structures in the base phase which is an oil phase, an S/O (Solid in Oil) type external skin preparation can be formed. The S/O type external skin preparation can be obtained by, for example, dispersing or dissolving the core-shell structures obtained by the aforesaid production process in an oil phase.

The base is not particularly limited, and can be appropriately selected from bases suitable for dispersing or dissolving the core-shell structures, according to the use purpose or the like.

A plurality of bases may be used in combination.

Examples of the bases include, but are not particularly limited to, vegetable oils, animal oils, neutral lipids, synthetic oils and fats, sterol derivatives, waxes, hydrocarbons, monoalcohol carboxylic acid esters, oxyacid esters, polyhydric alcohol fatty acid esters, silicones, higher (polyhydric) alcohols, higher fatty acids and fluorine-based oils.

Examples of the vegetable oils include, but are not particularly limited to, soybean oil, sesame oil, olive oil, coconut oil, palm oil, rice oil, cotton seed oil, sunflower oil, rice bran oil, cacao butter, cone oil, safflower oil and rapeseed oil.

Examples of the animal oils include, but are not particularly limited to, mink oil, turtle oil, fish oil, beef oil, horse oil, pig oil and shark squalane.

Examples of the neutral lipids include, but are not particularly limited to, triolein, trilinolein, trimyristin, tristearin and triarachidonin.

Examples of the synthetic oils and fats include, but are not particularly limited to, phospholipid and azone.

Examples of the sterol derivatives include, but are not particularly limited to, dihydrocholesterol, lanosterol, dihydrolanosterol, phytosterol, cholic acid and cholesteryl linoleate.

Examples of the waxes include candelilla wax, carnauba wax, rice wax, Japan wax, beeswax, montan wax, ozokerite, ceresin, paraffin wax, microcrystalline wax, petrolatum, Fischer-Tropsch wax, polyethylene wax and an ethylene/propylene copolymer.

Examples of the hydrocarbons include liquid paraffin (mineral oil), heavy liquid isoparaffin, light liquid isoparaffin, α-olefin oligomers, polyisobutene, hydrogenated polyisobutene, polybutene, squalane, olive-derived squalane, squalene, vaseline and solid paraffin.

Examples of the monoalcohol carboxylic acid esters include octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyloctyl sebacate, diisobutyl adipate, dioctyl succinate and triethyl citrate.

Examples of the oxyacid esters include cetyl lactate, diisostearyl malate and hydrogenated castor oil monoisostearate.

Examples of the polyhydric alcohol fatty acid esters include glyceryl trioctanoate, glyceryl trioleate, glyceryl triisostearate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate/eicosadioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, pentaerythrityl hydrogenated rosinate, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), (hexyldecanoic acid/sebacic acid) diglyceryl oligo ester, glycol distearate (ethylene glycol distearate), 3-methyl-1,5-pentanediol dineopentanoate and 2,4-diethyl-1,5-pentanediol dineopentanoate.

Examples of the silicones include dimethicone (dimethylpolysiloxane), highly polymerized dimethicone (highly polymerized dimethylpolysiloxane), cyclomethicone (cyclodimethylsiloxane, decamethylcyclopentasiloxane), phenyl trimethicone, diphenyl dimethicone, phenyl dimethicone, stearoxypropyl dimethylamine, (aminoethylaminopropyl methicone/dimethicone) copolymers, dimethiconol, dimethiconol crosspolymers, silicone resins, silicone rubber, amino-modified silicones such as aminopropyl dimethicone and amodimethicone, cation-modified silicones, polyether-modified silicones such as dimethicone copolyol, polyglycerol-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified or polyether-modified silicones, amino-modified or polyether-modified silicones, alkyl-modified or polyether-modified silicones, and polysiloxane/oxyalkylene copolymers.

Examples of the higher (polyhydric) alcohols include cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol and dimer diol.

Examples of the higher fatty acids include lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteisoheneicosanoic acid, long-chain branched fatty acid, dimer acid and hydrogenated dimer acid.

Examples of the fluorine-based oils include perfluorodecane, perfluorooctane and perfluoropolyether.

Examples of other bases include, but are not particularly limited to, bases used for ointment preparations and patch preparations, such as ointments, creams, aerosols, tapes, patches, poultices, gels and microneedles.

(External Skin Preparation)

The external skin preparation of the present invention can be used as any of external preparations, for example, ointment preparations and patch preparations, such as tapes (reservoir type, matrix type, etc.), ointments, lotions, aerosols, plasters, aqueous poultices, creams, gels, aerosols, patches and microneedles, without being limited thereto. The external skin preparation of the present invention may be of highly permeable systematic action type or local action type. The external skin preparation of the present invention may have sustainability for one day to one week, without being limited thereto, and in a preferred embodiment, the external skin preparation may be used in such a manner that it is applied once per day to per week.

The external skin preparation of the present invention may further contain other additive ingredients according to the dosage form and the use purpose thereof, etc. Examples of the additive ingredients include, but are not particularly limited to, an excipient, a colorant, a lubricant, a binder, an emulsifying agent, a thickener, a wetting agent, a stabilizing agent, a preservative, a solvent, a dissolution assisting agent, a suspending agent, a buffer, a pH adjustor, a gelling agent, a pressure-sensitive adhesive, an antioxidant, a transdermal absorption promoting agent, a stimulation reducing agent, an antiseptic, a chelating agent or a dispersant.

A case where the external skin preparation of the present invention contains the aforesaid core-shell structure will be described below.

In the external skin preparation of the present invention, the core-shell structure when the base phase is not contained, or the base phase containing the core-shell structure when the base phase is contained (both being sometimes collectively called "core-shell structure-containing basic ingredient" hereinafter) may be further dispersed in another ingredient. In this case, the external skin preparation of the present invention is provided by mixing/dispersing or emulsifying the core-shell structure-containing basic ingredient in an ingredient in which the core-shell structure-containing basic ingredient is not completely soluble. This can be appropriately selected according to the dosage form, and is not particularly limited. In order to provide the external skin preparation of the present invention as an ointment preparation or a patch preparation, such as ointment, cream, aerosol, tape, patch, poultice, gel or microneedle, the core-shell structure-containing basic ingredient can be, for example, mixed/dispersed or emulsified in the base or the like used for each dosage form.

A production process for the external skin preparation of the present invention is not particularly limited either. When the core-shell structure is used, the external skin preparation of the present invention can be produced in, for example, the following manner.

First, the core-shell structure can be produced in, for example, the following manner. The active ingredient, the solubilizing agent, and if desired, the additive ingredients, such as a release promoting agent, a stabilizing agent, a transdermal absorption promoting agent and a skin stimulation reducing agent, are dissolved in a solvent such as pure water or a phosphate buffer solution. To the resulting solution, a solution in which the surfactant, and if desired, the additive ingredients, such as a release promoting agent, a skin stimulation reducing agent, an analgesic, a transdermal absorption promoting agent and a stabilizing agent, are dissolved in a solvent such as cyclohexane, hexane or toluene is added, and they are stirred with a homogenizer. Thereafter, the resulting solution is subjected to freeze drying, whereby the core-shell structure can be prepared.

Using the core-shell structure, the external skin preparation can be produced by, for example, a solution coating method. In the solution coating method, the core-shell structure and the base, and if desired, the additive ingredients such as a transdermal absorption promoting agent, a thickener and a gelling agent are added to a solvent such as hexane, toluene or ethyl acetate in such a manner that predetermined ratios are obtained, and then the mixture is stirred to prepare a homogeneous solution. A solid content of the solution is preferably 10 to 80 mass %, more preferably 20 to 60 mass %.

Next, the solution containing the ingredients is uniformly applied onto a release liner (siliconized polyester film or the like) using a coating machine such as a knife coater, a comma coater or a reverse coater and dried to form a drug-containing layer, and on this layer, a support is laminated, whereby a transdermal absorption type external skin preparation can be obtained. Depending on the type of the support, after the drug-containing layer is formed on the support, a release liner may be laminated on the surface of the drug-containing layer.

In another method, for example, the base and the additive ingredients such as a transdermal absorption promoting agent, a stabilizing agent, a thickener and a gelling agent are added to the core-shell structure, when needed, and they are mixed. The resulting mixture is retained by lamination or impregnation of a natural fabric member such as gauze or absorbent cotton, a synthetic fiber fabric member such as polyester or polyethylene, or a woven fabric, a non-woven fabric or the like produced by appropriately combining the above materials, or a permeable membrane or the like, according to the application. Furthermore, the mixture retained can be covered with a pressure-sensitive adhesive cover material or the like and used.

The transdermal absorption type external skin preparation obtained as above is appropriately cut into a shape of an ellipse, a circle, a square, a rectangle or the like according to the application. Moreover, a pressure-sensitive adhesive layer or the like may be provided on the periphery of the external skin preparation, when needed.

Next, the present invention will be clarified by reference to the specific examples of the present invention and the comparative examples. It should be construed that the present invention is in no way limited to the following examples.

Example 1

A mixture of 37.8 g of pure water (Milli-Q water), 4.2 g of 1.0 mol/L hydrochloric acid (manufactured by Wako Pure Chemical Industries, Ltd., trade name "1 mol/L Hydrochloric Acid") and 18.0 g of methanol (manufactured by Wako Pure Chemical Industries, Ltd.) was used as a solvent (A). To 50 g of the solvent (A), 0.5 g of aripiprazole as a poorly water-soluble active ingredient (drug) and 2.5 g of β-cyclodextrin (β-CD) as a solubilizing agent were added, and they were stirred at room temperature for 1 hour. Thereafter, the resulting mixture was subjected to freeze drying for 2 days to obtain a solubilizable product. To 880 mg of pure water, 120 mg of the resulting solubilizable product was added, and mixing and dispersing were carried out to prepare an external skin preparation. As the aripiprazole, aripiprazole manufactured by Tokyo Chemical Industry Co., Ltd. and having a weight-average molecular weight of 448 g/mol and an octanol/water partition coefficient of 4.5 was used. As the β-cyclodextrin, trade name "β-Cyclodextrin" manufactured by Tokyo Chemical Industry Co., Ltd. and having a molecular weight of 1135 g/mol was used.

Example 2

An external skin preparation was prepared in the same manner as in Example 1, except that instead of the β-cyclodextrin (β-CD, manufactured by Tokyo Chemical Industry Co., Ltd., trade name "β-Cyclodextrin"), sucrose laurate (manufactured by Mitsubishi Chemical Foods Corporation, trade name "RYOTO Sugar Ester L1695", molecular weight: 630 g/mol) was used as the solubilizing agent.

Comparative Example 1

To 980 mg of pure water, 20 mg of aripiprazole (manufactured by Tokyo Chemical Industry Co., Ltd., molecular weight: 448 g/mol, octanol/water partition coefficient: 4.5) was added, and mixing and dispersing were carried out to prepare an external skin preparation.

(Evaluation)

Permeability Test on Hairless Rat Skin (without Stratum Corneum);

In a cell for a test of drug permeation into the skin (FIG. 1), hairless rat skin (Japan SLC, Inc., taken out from 8-week-old HWY/Sic) from which the stratum corneum had been removed in advance by tape stripping was set. To the upper part of this device, 1000 mg (about 7 cm$^2$) of the external skin preparation produced in Example 1 or 2 or Comparative Example 1 was applied. In a receptor layer at the lower part was introduced a buffer solution containing 0.01 M of $K_2PO_4$, 0.15 M of NaCl and 10 ppm of gentamicin sulfate (manufactured by Wako Pure Chemical Industries, Ltd., G1658) in distilled water, the pH of the solution being adjusted to 4.0 with phosphoric acid. The device was placed in a thermostatic chamber kept at 32° C. since the start of the test. At a predetermined time after the test was started, 1 ml of the solution in the thermostatic chamber was taken out from the receptor layer at the lower part, and immediately afterwards 1 ml of a solution having the same composition was added to the layer. To each of the receptor solution samples collected, methanol was added to extract lipid eluted or the like, and the extract was centrifuged. After the centrifugation, the concentration of the active ingredient in the supernatant was determined by high-performance liquid chromatography (HPLC). On the basis of the amount of the active ingredient determined, the cumulative amount of permeation into the skin over a period of 24 hours was calculated.

The results are set forth in Table 1 below. In Table 1, solubilities of the poorly water-soluble active ingredients having been solubilized by the solubilizing agent in Examples 1 and 2, in pure water at 25° C. and solubility of the poorly water-soluble active ingredient itself of Comparative Example 1 in pure water at 25° C. are also set forth together. For determination of the solubility, solutions at concentrations of 1%, 0.1%, 0.01% and 0.001% were prepared, and the concentration at which the solid component was not visually observed was regarded as a solubility. In Table 1, the ratios of permeation into the skin from which the stratum corneum has been removed, that is, utilization ratios of the active ingredient are also set forth together.

TABLE 1

| | | Dose of drug (mg) | Dose of preparation (external skin preparation) (mg) | Base | Stratum corneum | Cumulative amount of permeation (μg/cm²/24 hr) | Solubility | Utilization ratio |
|---|---|---|---|---|---|---|---|---|
| Example 1 | β-CD solubilizable product | 20 | 1000 | Milli-Q water | no | 1458.0 | 1 mass % | 53% |
| Example 2 | L1695 solubilizable product | 20 | 1000 | | | 147.0 | 1 mass % | 6% |
| Comparative example 1 | drug only | 20 | 1000 | | | 6.6 | not more than 0.01 mass % | 0.25% |
| Reference example 1 | β-CD solubilizable product | 20 | 1000 | | yes | 6.1 | 1 mass % | — |
| Reference example 2 | L1695 solubilizable product | 20 | 1000 | | | 1.1 | 1 mass % | — |
| Reference example 3 | drug only | 20 | 1000 | | | 0.7 | not more than 0.01 mass % | — |

In Table 1, the results in Reference Examples 1 to 3, i.e., the results obtained when hairless rat skin from which the stratum corneum had not been removed (with stratum corneum) was used in a test in otherwise the same manner as in the permeability test on hairless rat skin are also set forth together. In Reference Example 1, the external skin preparation of Example 1 was used, and in Reference Example 2, the external skin preparation of Example 2 was used. In Reference Example 3, the external skin preparation of Comparative Example 1 was used.

Example 3

In 10 g of the solvent (A), 50 mg of aripiprazole (manufactured by Tokyo Chemical Industry Co., Ltd., weight-average molecular weight: 448 g/mol, octanol/water partition coefficient: 4.5) as a poorly water-soluble active ingredient (drug) and 250 mg of β-cyclodextrin β-CD, manufactured by Tokyo Chemical Industry Co., Ltd., trade name "β-Cyclodextrin") as a solubilizing agent were dissolved. To the resulting solution, a solution obtained by dissolving 750 mg of glyceryl monocaprylate (manufactured by Taiyo Kagaku Co., Ltd., trade name "Sunsoft No. 700P-2-C", HLB value: 10.9) as a surfactant in 20 g of cyclohexane was added, and they were stirred with a homogenizer (25000 rpm). Thereafter, the resulting mixture was subjected to freeze drying for 2 days to obtain a core-shell structure having core-shell constitution containing the active ingredient in the core portion and containing the surfactant in the shell portion. To 580 mg of liquid paraffin (manufactured by Wako Pure Chemical Industries, Ltd., density: 0.800 to 0.835 g/ml), 420 mg of the resulting core-shell structure was added, and mixing and dispersing were carried out to prepare an external skin preparation.

Example 4

An external skin preparation was prepared in the same manner as in Example 3, except that in addition to the aripiprazole and the β-cyclodextrin, 25 mg of lactic acid (manufactured by Wako Pure Chemical Industries, Ltd., solubility in water: 100%) as a release promoting agent was dissolved in the solvent (A).

Example 5

An external skin preparation was prepared in the same manner as in Example 4, except that instead of the β-cyclodextrin (β-CD, manufactured by Tokyo Chemical Industry Co., Ltd., trade name "β-Cyclodextrin"), sucrose laurate (manufactured by MITSUBISHI—CHEMICAL FOODS CORPORATION, trade name "RYOTO Sugar Ester L1695") was used as the solubilizing agent.

Example 6

An external skin preparation was prepared in the same manner as in Example 4, except that instead of the β-cyclodextrin (β-CD, manufactured by Tokyo Chemical Industry Co., Ltd., trade name "β-Cyclodextrin"), cycloamylose (manufactured by Glico Nutrition Co., Ltd., trade name "Cycloamylose", molecular weight: 7000 g/mol) was used as the solubilizing agent.

Comparative Example 2

To 980 mg of liquid paraffin (manufactured by Wako Pure Chemical Industries, Ltd., density: 0.800 to 0.835 g/ml), 20 mg of aripiprazole (manufactured by Tokyo Chemical Industry Co., Ltd., weight-average molecular weight: 448 g/mol, octanol/water partition coefficient: 4.5) was added, and mixing and dispersing were carried out to prepare an external skin preparation.

Comparative Example 3

An external skin preparation was prepared in the same manner as in Example 3, except that the β-cyclodextrin was not used as the solubilizing agent.

Comparative Example 4

An external skin preparation was prepared in the same manner as in Example 4, except that the β-cyclodextrin was not used as the solubilizing agent.

Example 7

In 9.8 g of water, 50 mg of sulfasalazine (manufactured by Tokyo Chemical Industry Co., Ltd., molecular weight: 398 g/mol, octanol/water partition coefficient: 2.3) as a poorly water-soluble active ingredient (drug), 150 mg of hypromellose acetate succinate (manufactured by Shin-Etsu Chemical Co., Ltd., trade name "AQOAT-AS-LG", molecular weight: 20000 g/mol) as a solubilizing agent and 50 mg of sodium hydroxide (NaOH, manufactured by Wako Pure Chemical Industries, Ltd., solubility in water: not less than 10%) as a release promoting agent were dissolved. To the resulting solution, a solution obtained by dissolving 750 mg of glyceryl monocaprylate (manufactured by Taiyo Kagaku Co., Ltd., trade name "Sunsoft No. 700P-2-C", HLB value: 10.9) as a surfactant in 19.3 g of cyclohexane was added, and they were stirred with a homogenizer (25000 rpm). Thereafter, the resulting mixture was subjected to freeze drying for 2 days to obtain a core-shell structure having core-shell constitution containing the active ingredient in the core portion and containing the surfactant in the shell portion. To 636 mg of liquid paraffin (manufactured by Wako Pure Chemical Industries, Ltd., density: 0.800 to 0.835 g/ml), 424 mg of the resulting core-shell structure was added, and mixing and dispersing were carried out to prepare an external skin preparation.

Example 8

An external skin preparation was prepared in the same manner as in Example 7, except that instead of the glyceryl monocaprylate, glyceryl monolaurate (manufactured by Taiyo Kagaku Co., Ltd., trade name "Sunsoft No. 750-C", HLB value: 8.7) was used as the surfactant.

Example 9

An external skin preparation was prepared in the same manner as in Example 7, except that instead of the glyceryl monocaprylate, glyceryl monocaprate (manufactured by Taiyo Kagaku Co., Ltd., trade name "Sunsoft No. 760-C", HLB value: 9.7) was used as the surfactant.

Comparative Example 5

To 1039 mg of liquid paraffin (manufactured by Wako Pure Chemical Industries, Ltd., density: 0.800 to 0.835 g/ml), 21 mg of sulfasalazine (manufactured by Tokyo Chemical Industry Co., Ltd., weight-average molecular weight: 398 g/mol, octanol/water partition coefficient: 2.3) was added, and mixing and dispersing were carried out to prepare an external skin preparation.

Comparative Example 6

An external skin preparation was prepared in the same manner as in Example 9, except that the solubilizing agent and the release promoting agent were not used.

Example 10

In 10 g of a solvent (water), 50 mg of aripiprazole (manufactured by Tokyo Chemical Industry Co., Ltd., weight-average molecular weight: 448 g/mol, octanol/water partition coefficient: 4.5) as a poorly water-soluble active ingredient (drug), 25 mg of gallic acid (manufactured by Tokyo Chemical Industry Co., Ltd., trade name "Gallic Acid Hydrate", molecular weight: 170 g/mol) as a solubilizing agent and 25 mg of tartaric acid (manufactured by Wako Pure Chemical Industries, Ltd., solubility in water: not less than 10%) as a release promoting agent were dissolved. To the resulting solution, a solution obtained by dissolving 600 mg of glyceryl monocaprylate (C8 shell, manufactured by Taiyo Kagaku Co., Ltd., trade name "Sunsoft No. 700P-2-C", HLB value: 10.9) as a surfactant in 20 g of cyclohexane was added, and they were stirred with a homogenizer (25000 rpm). Thereafter, the resulting mixture was subjected to freeze drying for 2 days to obtain a core-shell structure having core-shell constitution containing the active ingredient in the core portion and containing the surfactant in the shell portion. To 630 mg of liquid paraffin (manufactured by Wako Pure Chemical Industries, Ltd., density: 0.800 to 0.835 g/ml), 270 mg of the resulting core-shell structure was added, and mixing and dispersing were carried out to prepare an external skin preparation.

Example 11

An external skin preparation was prepared in the same manner as in Example 10, except that instead of the gallic acid (manufactured by Tokyo Chemical Industry Co., Ltd., trade name "Gallic Acid Hydrate") as the solubilizing agent, 4-aminobenzoic acid (manufactured by Tokyo Chemical Industry Co., Ltd., trade name "4-Aminobenzoic Acid", molecular weight: 137 g/mol) was used.

Comparative Example 7

An external skin preparation was prepared in the same manner as in Example 10, except that the solubilizing agent was not used.

(Evaluation)

Permeability Test on Hairless Rat Skin (with Stratum Corneum);

In a cell for a test of drug permeation into the skin (FIG. 1), hairless rat skin (Japan SLC, Inc., taken out from 8-week-old HWY/Slc) was set. To the upper part of this device, 1000 mg (about 7 cm$^2$) of any one of the external skin preparations produced in Examples 3 to 5 and Comparative Examples 2 to 4 was applied. In a receptor layer at the lower part was introduced a buffer solution containing 0.01 M of $K_2PO_4$, 0.15 M of NaCl and 10 ppm of gentamicin sulfate (manufactured by Wako Pure Chemical Industries, Ltd., G1658) in distilled water, the pH of the solution being adjusted to 4.0 with phosphoric acid. The device was placed in a thermostatic chamber kept at 32° C. since the start of the test. At a predetermined time after the test was started, 1 ml of the solution in the thermostatic chamber was taken out from the receptor layer at the lower part, and immediately afterwards 1 ml of a solution having the same composition was added to the layer. To each of the receptor solution samples collected, methanol was added to extract lipid eluted or the like, and the extract was centrifuged. After the centrifugation, the concentration of the active ingredient in the supernatant was determined by high-performance liquid chromatography (HPLC). On the basis of the amount of the active ingredient determined, the cumulative amounts of permeation into the skin over a period of 17.5 hours, a period of 21 hours and a period of 24 hours were calculated. Moreover, a flux between 17.5 hours and 24 hours was determined.

The results of Example 3 to 6 and Comparative Examples 2 to 4 are shown in FIG. 2 and Table 2 below. In Table 2, solubilities of the poorly water-soluble active ingredients having been solubilized by the solubilizing agent in Examples 3 to 6, in pure water at 25° C. and solubilities of the poorly water-soluble active ingredients themselves of Comparative Examples 2 to 4 in pure water at 25° C. are also set forth together.

The results of Example 7 to 9 and Comparative Examples 5 and 6 are shown in FIG. 3 and Table 3 below. In Table 3, solubilities of the poorly water-soluble active ingredients having been solubilized by the solubilizing agent in Examples 7 to 9, in pure water at 25° C. and solubilities of the poorly water-soluble active ingredients themselves of Comparative Examples 5 and 6 in pure water at 25° C. are also set forth together.

The results of Examples 10 and 11 and Comparative Example 7 are shown in FIG. 4 and Table 4 below. In Table 4, solubilities of the poorly water-soluble active ingredients having been solubilized by the solubilizing agent in Examples 10 and 11, in pure water at 25° C. and solubility of the poorly water-soluble active ingredient itself of Comparative Example 7 in pure water at 25° C. are also set forth together.

TABLE 2

| | | Solubilizing agent | Release promoting agent | Dose of drug (mg) | Dose of preparation (external skin preparation) (mg) | Base | Stratum corneum | Cumulative amount of permeation ($\mu g/cm^2/24$ hr) | Flux ($\mu g/cm^2/hr$) | Solubility |
|---|---|---|---|---|---|---|---|---|---|---|
| Example 3 | aripiprazole:β-CD:700P-2-C = 1:5:15 | β-CD | — | 20 | 1000 | liquid paraffin | yes | 46.6 | 2.3 | 1 mass % |
| Example 4 | aripiprazole:β-CD:lactic acid:700P-2-C = 1:5:0.5:15 | β-CD | lactic acid | 20 | 1000 | | | 79.8 | 4.6 | 1 mass % |
| Example 5 | aripiprazole:L1695:lactic acid:700P-2-C = 1:5:0.5:15 | L1695 | lactic acid | 20 | 1000 | | | 34.1 | 1.9 | 1 mass % |
| Example 6 | aripiprazole:cycloamylose:lactic acid:700P-2-C = 1:5:0.5:15 | cycloamylose | lactic acid | 20 | 1000 | | | 73.5 | 4.5 | 1 mass % |
| Comparative example 2 | drug only | — | — | 20 | 1000 | | | 1.1 | 0.1 | not more than 0.01 mass % |
| Comparative example 3 | aripiprazole:700P-2-C = 1:15 | — | — | 20 | 1000 | | | 24.3 | 1.5 | not more than 0.01 mass % |
| Comparative example 4 | aripiprazole:lactic acid:700P-2-C = 1:0.5:15 | — | lactic acid | 20 | 1000 | | | 28.7 | 1.7 | not more than 0.01 mass % |

TABLE 3

| | | Solubilizing agent | Release promoting agent | Dose of drug (mg) | Dose of preparation (external skin preparation) (mg) | Base | Stratum corneum | Cumulative amount of permeation ($\mu g/cm^2/24$ hr) | Flux ($\mu g/cm^2/hr$) | Solubility |
|---|---|---|---|---|---|---|---|---|---|---|
| Example 7 | sulfasalazine:AQOAT-AS-LG:NaOH:700P2C = 1:3:1:15 | AGOAT-AS-LG | NaOH | 21 | 1060 | liquid paraffin | yes | 9855 | 1176 | 1 mass % |
| Example 8 | sulfasalazine:AQOAT-AS-LG:NaOH:750C = 1:3:1:15 | AQOAT-AS-LG | NaOH | 21 | 1060 | | | 5576 | 356 | 1 mass % |
| Example 9 | sulfasalazine:AQOAT-AS-LG:NaOH:760C = 1:3:1:15 | AQOAT-AS-LG | NaOH | 21 | 1060 | | | 6251 | 437 | 1 mass % |
| Comparative example 5 | sulfasalazine only | — | — | 21 | 1060 | | | 0 | 0 | not more than 0.01 mass % |
| Comparative example 6 | sulfasalazine:760C = 1:15 | — | — | 21 | 1060 | | | 5109 | 146 | not more than 0.01 mass % |

TABLE 4

|  | Solubilizing agent | Dose of drug (mg) | Dose of preparation (external skin preparation) (mg) | Base | Stratum corneum | Cumulative amount of permeation (µg/cm²/24 hr) | Flux (µg/cm²/hr) | Solubility |
|---|---|---|---|---|---|---|---|---|
| Example 10 | aripiprazole:tartaric acid:gallic acid:C8 shell = 1:0.5:0.5:12 | gallic acid | 18 mg | 900 mg | | | 131.6 | 7.5 | 0.1 mass % |
| Example 11 | aripiprazole:tartaric acid:4-aminobenzoic acid:C8 shell = 1:0.5:0.5:12 | 4-aminobenzoic acid | 18 mg | 900 mg | liquid paraffin | yes | 138.5 | 7.7 | 0.1 mass % |
| Comparative example 7 | aripiprazole:tartaric acid:C8 shell = 1:0.5:12 | none | 18 mg | 900 mg | | | 14.6 | 1.3 | not more than 0.01 mass % |

Examples 12 and 13, and Comparative Example 8

In Examples 12 and 13 and Comparative Example 8, an evaluation example for imitating a microneedle was carried out, in which into hairless rat skin from which the stratum corneum had not been removed, 0.05 ml of the external skin preparation was injected with a 1 mL syringe having a syringe needle of 27 G, at each of 10 sites in a depth of 0.3 to 0.5 mm. In Example 12, the external skin preparation of Example 1 was used, and in Example 13, the external skin preparation of Example 2 was used. In Comparative Example 8, the external skin preparation of Comparative Example 1 was used.

In Examples 12 and 13 and Comparative Example 8, the cumulative amount of permeation into the skin (with stratum corneum) over a period of 24 hours was determined using hairless rat skin from which the stratum corneum had not been removed in the permeability test on the hairless rat skin, similarly to Reference Examples 1 to 3. The results are set forth in Table 5 below.

TABLE 5

|  | | Dose of drug (mg) | Dose of preparation (external skin preparation) (mg) | Base | Stratum corneum | Cumulative amount of permeation (µg/cm²/24 hr) | Solubility |
|---|---|---|---|---|---|---|---|
| Example 12 | β-CD solubilizable product | 20 | 50 µL × 10 sites | Milli-Q water | yes | 422.3 | 1 mass % |
| Example 13 | L1695 solubilizable product | 20 | 50 µL × 10 sites | | | 51.8 | 1 mass % |
| Comparative example 8 | drug only | 20 | 50 µL × 10 sites | | | 2.6 | not more than 0.01 mass % |

REFERENCE SIGNS LIST

1 Parafilm
2 Skin
3 Patch preparation
4 Receptor solution (pH=7.2, phosphate buffer solution)
5 Stirrer
10 Core-shell structure
11 Core portion
12 Shell portion

The invention claimed is:

1. An external skin preparation containing a core-shell structure, comprising:

a core portion containing a poorly water-soluble active ingredient and a solubilizing agent, and a shell portion containing a surfactant, wherein the solubilizing agent is at least one selected from the group consisting of cyclodextrin, methyl-cyclodextrin, dimethyl-cyclodextrin, 2-hydroxypropyl-cyclodextrin, hydroxyethyl-cyclodextrin, sulfobutyl ether-cyclodextrin, glucosyl-cyclodextrin, maltosyl-cyclodextrin and cluster dextrin, the surfactant is at least one selected from the group consisting of glycerol fatty acid esters, sorbitan fatty acid esters, propylene glycol fatty acid esters and fatty acid alkanolamides, and a mass ratio between the poorly water-soluble active ingredient and the solubilizing agent (poorly water-soluble active ingredient:solubilizing agent) is 1:0.1 to 1:30.

2. The external skin preparation according to claim 1, further comprising a release promoting agent for promoting release of the poorly water-soluble active ingredient.

* * * * *